United States Patent [19]

Borrevang et al.

[11] 4,051,133

[45] Sept. 27, 1977

[54] PROCESS FOR CONVERTING PENICILLIN SULFOXIDES TO THE CORRESPONDING 3-DESACETOXYCEPHALOSPORINS

[75] Inventors: Poul Borrevang, Rodovre; Henning Borge Petersen, Lyngby, both of Denmark

[73] Assignee: Novo Industri A/S, Bagsvaerd, Denmark

[21] Appl. No.: 646,321

[22] Filed: Jan. 2, 1976

[30] Foreign Application Priority Data

Jan. 3, 1975 United Kingdom .................. 307/75

[51] Int. Cl.$^2$ ............................................. C07D 501/10
[52] U.S. Cl. ..................................... 544/18; 424/246; 260/239.1
[58] Field of Search ..................................... 260/243 C

[56] References Cited

U.S. PATENT DOCUMENTS

| 3,852,295 | 12/1974 | Graham et al. | 260/243 C |
| 3,935,198 | 1/1976 | Murakami et al. | 260/243 C |
| 3,936,447 | 2/1976 | Petersen et al. | 260/243 C |

*Primary Examiner*—Nicholas S. Rizzo
*Attorney, Agent, or Firm*—Fidelman, Wolffe & Waldron

[57] ABSTRACT

Conversion of penicillin sulfoxides to the corresponding 3-desacetoxycelphalosporins are carried out in high yield by heating, e.g. 80°–130° C, a solvent solution of the penicillin in the presence of a complex formed by a phosphite or phosphine amide with the salt of a strong acid and a nitrogenous base, e.g. alpha-picoline hydrobromide.

One preferred amide is 2-piperidino-1,3,2-dioxaphospolane.

8 Claims, No Drawings

PROCESS FOR CONVERTING PENICILLIN SULFOXIDES TO THE CORRESPONDING 3-DESACETOXYCEPHALOSPORINS

INTRODUCTION

This invention relates to a process of converting penicillin sulfoxide derivatives into the corresponding derivatives of 3-desacetoxycephalosporin.

This type of process is described in J.A.C.S. 85 (1963), page 1896. According to the prior art this conversion reaction is carried out under acid conditions while heating. However, the yield obtained by the process is small.

The process can be improved substantially by changing the reaction conditions used.

THE INVENTION

Surprisingly, it has now been found that a high purity product can be obtained in high yields by using as the catalyst a complex formed by adding phosphate amides or phosphine amides (hereinafter referred to as P(III)-amides) to slightly acidic or neutral substances, optionally in the presence of a tertiary amine.

This discovery is believed to be surprising because it appears from the literature that phosphites and phosphines (when heated) convert penicillin sulfoxides into thiazolineazetidinones (Flynn: Cephalosporins and Penicillins, Academic Press 1972, page 200, and the references mentioned in said article). In most cases, that reaction is completely avoided when the conversion is effected by the process of the invention, and the valuable 3-desacetoxycephalosporins are obtained.

DETAILED PRACTICE OF THE INVENTION

The reaction time used by the process of this invention is normally shorter than that of the prior art processes, and consequently, the thermal decomposition which may be significant in the prior art processes can be reduced. Thermal decomposition may result in colored products, the purification of which is difficult to perform in a satisfactory manner.

By using a catalyst comprising P(III)-amides, the products obtained are so pure that a spontaneous crystallization of a colorless substance may be observed, when the reaction mixture is concentrated after completion of the reaction.

The reaction in which a penicillin sulfoxide is converted into a 3-desacetoxycephalosporin may be illustrated by the following reaction scheme:

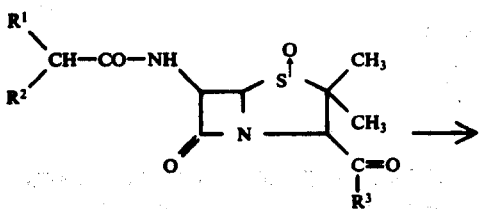

I

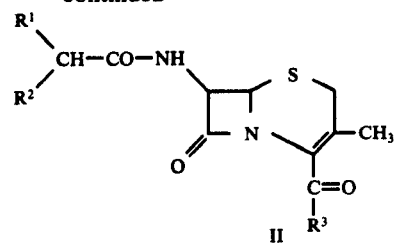

II wherein
R¹ is selected from the group consisting of a hydrogen atom, a substituted or non-substituted alkyl, aryl, or aryloxy group;
R² is selected from the group consisting of a hydrogen atom, an alkyl group containing 1-4 carbon atoms, or an amino group which is protected with a protecting group;
R³ is a carboxylic acid protecting group, e.g. an amide or an ester. Examples of suitable amides are saccharimide, anilide, succinimide and phthalimide. Examples of suitable esters are p-nitrobenzyl, 2-trichloroethyl, benzohydryl, p-methoxybenzyl, p-bromophenacyl, 9-fluoroenyl, and cyanomethyl esters.

Penicillin sulfoxides having the formula I can be prepared by methods which are well known in the literature, i.e. by oxidation of the corresponding penicillins, and by subsequently protecting the carboxylic acid group, or by protecting the carboxylic acid groups in penicillins first, and subsequently oxidizing said compounds.

Preferred penicillins are fermentation penicillins, such as penicillin G and penicillin V, as well as semisynthetic penicillins prepared by acylating 6-aminopenicillanic acid derivatives preferably with an acyl group which after completion of the process of this invention and the removal of protecting groups, if any, produces a valuable antibiotic cephalosporin having the formula II in which R³ is OH.

Both the starting penicillin compounds and the product cephalosporin compounds are believed to be known to the art and per se form no part of this invention.

The P(III)-amides employed for the process of this invention are illustrated by the formula III:

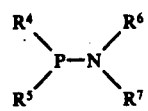

III wherein R⁴ and R⁵ are the same or different or together form a carbocyclic or heterocyclic ring which may be substituted or non-substituted, or are part of a polycyclic system, and are selected from the group consisting of substituted or non-substituted alkyl, cycloalkyl, aryl, aralkyl, alkoxy, cycloalkoxy, aryloxy, aralkoxy, dialkylamino, diarylamino, and aralkylamino groups, and N-heterocyclic rings. Examples of preferred groups are ethoxy, phenyl, dimethylamino groups, and groups in which R⁴,R⁵ and P form the ring systems:

IV

-continued

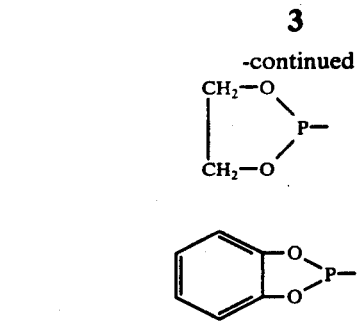

wherein R[6] and R[7] are similar or different, or together with N form a ring which may be substituted in one or more positions, and are selected from the group of unsubstituted or substituted alkyl, cycloalkyl, aralkyl, aryl, trialkylsilyl groups, or groups in which R[6] and R[7] together with N form a ring with one or more other hetero atoms.

Preferred groups are methyl, isopropyl, and trimethylsilyl groups as well as piperidine, 2,6-dimethylpiperidine, morpholine, pyrrol, and pyrrolidine rings.

Preferred P(III)-amides are the following:
2-piperidino-1,3,2-dioxaphospholane,
2-diisopropylamino-1,3,2-dioxaphospholane,
2-morpholino-1,3,2-dioxaphospholane,
2-pyrrolidino-1,3,2-dioxaphospholane,
2-pyrrolo-1,3,2-dioxaphospholane,
2-di(trimethylsilyl) amino-1,3,2-dioxaphospholane,
Piperidino-diphenylphosphine,
2-piperidino-4,5-benzo-1,3,2-dioxaphospholane,
2-(2',6'-dimethylpiperidino)-4,5-benzo-1,3,2-dioxaphospholane
2-(1'-imidazolyl)-4,5-benzo-1,3,2-dioxaphospholane,
tris-(dimethylamino)-phosphine.

As has been alluded to above, the P(III)-amides form complexes with slightly acidic or essentially neutral compounds. It is preferred to use salts of strong acids and nitrogeneous bases. If desired, an excess of the base may be used.

Preferred acids are hydrogen bromide, sulfonic acids such as methane sulfonic acid, phosphoric acid, phosphonic acid, and phosphoric acid monoalkyl esters, such as trichloroethyl phosphoric acid. Examples of preferred bases ae pyridine, substituted pyridines such as picolines and lutidines, dimethylaniline and quinoline.

The salt may be performed, or may be formed in situ by mixing predetermined amounts of acid and base.

Spectroscopic investigations have shown that the P(III)-amide forms a complex with the added salt. This has been shown by recording $^1$H and $^{31}$P-NMR spectra of the mixtures and is most clearly evidenced by the $^{31}$P-spectra in which clear changes in the "chemical shift" for phosphorus by adding a mixture of acid and base to the P(III)-amide have been observed.

Table I sets forth the "chemical shift" obtained by $^{31}$P-NMR-spectroscopy for P(III)-amides, and for typical catalyst complexes comprising said P(III)-amides.

Table I

| | Chemical shift measured at 36.4 MHz in CDCl₃ with 85% H₃PO₄ as standard. |
|---|---|
| 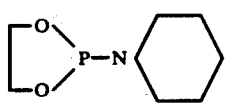 | −138 ppm |
| (same structure) + 2 HBr | −135 ppm |
| (dioxaphospholane-N-piperidine) + 1 CH₃SO₃H + 1 N-methylpyridine | −135 ppm |
| diphenylphosphino-cyclohexylamine | −62.6 ppm |
| diphenylphosphino-cyclohexylamine + 1 HBr + 1 N-methylpyridine | −53.7 ppm |
| diphenylphosphino-cyclohexylamine + 1 CH₃SO₃H + 1 N-methylpyridine | −29.5 ppm |

Table II sets forth the results obtained by conductivity measurements in dry methylene chloride for various catalysts.

Table II

| | Contents per 50 ml methylene chloride | Conductivity, micromho/cm |
|---|---|---|
| A: | 3.25 millimoles piperidino-dioxaphospholane | 0.8 |
| B: | 6.50 millimoles α-picoline, hydrobromide, and 3.25 millimoles α-picoline | 34.3 |
| C: | A + B | 29.2 |

It has been concluded from the above results that the above-mentioned compounds form a complex.

This will also appear from the fact that if the compounds are used alone, i.e. the P(III)-amide alone or the salt alone for conversion of penicillins to cephalosporin derivatives, significantly smaller yields are obtained.

The conversion of the penicillin sulfoxide (I) into the 3-desacetoxycephalosporin (II) is preferably carried out by dissolving the penicillin sulfoxide in an inert solvent, or in a mixture of solvents having a suitable boiling point range, i.e., between 80° and 130° C. Preferred solvents are dioxane, toluene, and methylisobutylketone.

The compounds which form the catalyst complex are added to this solution either in a mixture or separately. Normally, the P(III)-amide is used in an amount of 0.04 - 0.25 mole equivalents, and the salt in an amount of between 0.05 and 0.4 mole equivalents. If desired, the nitrogenous) base may be used in an excess up to 0.30 mole equivalent.

A particularly advantageous mixture consists of 0.1 mole P(III)-amide, 0.2 mole acid, and 0.3 mole base per mole penicillin sulfoxide.

The reaction mixture is heated under refluxing, and the reflux is passed through a suitable siccative, such as aluminum oxide, calcium oxide, sodium hydroxide, calcium chloride, or a molecular sieve to remove water. The water may also be separated in a distillation column.

When the starting material, catalyst, and the reaction temperature is properly selected, the reaction process is completed in 4-8 hours. The reaction is normally followed on T.L.C. and is discontinued when the starting material has been completely converted. Mixtures of benzene and ethyl acetate are normally suitable as eluating agents.

Further treatment of the reaction mixture depends on the solvent used. In most cases, the product (II) is separated by a spontaneous crystallization when the reaction mixture is concentrated. Water or a mixture of water and alcohol may be added to the reaction mixture, when the solvent used is miscible with water or solvent mixture.

In case of less pure reaction mixtures, the product may be purified by extraction and crystallized in a suitable solvent, (the selection of which depends on the starting materials used).

The product (II) may be further treated by well-known methods, e.g., removal of protecting groups, and may be converted to a valuable cephalosporin antibiotic. When an appropriate penicillin ester has been used as starting material, the product obtained by the process of the invention may itself be an active antibiotic.

The invention will now be described in further detail with reference to the following examples.

EXAMPLE 1

Trichloroethyl-3-methyl-7-phenylacetamido-ceph-3-em-4-carboxylate.

0.45 ml of a 2.2N methylene chloride solution of α-picoline-hydrobromide (1 millimole), 0.10 ml (1 millimole) of α-picoline, and 0.21 ml (1.4 millimole) of 2-piperidino-1,3,2-dioxaphospholane were added to a solution of 2.4 g (5 millimoles) of penicillin-G-sulfoxide-trichloroethyl-ester in 70 ml dry dioxane.

The solution thus prepared was refluxed, and the reflux was passed through 35 g basic aluminum oxide. T.L.C. indicated that the starting material had been completely converted after a period of 5 ¼ hours.

The heating was stopped, and the major portion of the solvent was removed at room temperature in vacuum. 50 ml of ethylacetate was added, and the mixture was washed twice with 50 ml water. The organic phase was dried over magnesium sulfate and evaporated to dryness. The crude product contains the desired cephalosporin ester in an amount corresponding to 57% of the theoretical amount as determined by NMR-spectroscopy of the crude product. The pure ester was prepared by crystallization from a slurry in 70% isopropanol. Melting point: 160° - 161° C.

NMR (CDCl$_3$): 7.30 (s, 5H), 6.4 (d, 1H) $J_{HNCH}$= 9.3 Hz, 5.78 (dd, 1H) $J_{HNCH}$= 9.3 Hz, $J_{HCCH}$=4.5 Hz, 4.95 (d, 1H) J = 4.5 Hz, 4.84 (AB, 2H), 3.60 (S, 2H), 3.33 (AB, 2H), 2.15 (s, 3H).

IR (KBr): 3320 cm$^{-1}$ (NH band), 1765 cm$^{-1}$ (β-lactame CO), 1725 cm$^{-1}$ (ester CO), 1670 cm$^{-1}$ (amide I), 1530 cm $^{-1}$ (amide II).

Analysis: Calculated for C$_{18}$H$_{17}$O$_4$N$_2$SCl$_3$ C: 46.62%; H: 3.70%; N: 6.04%; S: 6.91%; Cl: 22.94% Found: C: 46.56%; H: 3,77%; N: 5.99%; S: 6.90%; Cl: 22.65%

EXAMPLE 2

Trichloroethyl-3-methyl-7-phenylacetamido-ceph-3-em-4-carboxylate.

0.45 ml of a 2,2N methylene chloride solution of α-picoline-hydrobromide (1 millimole) and 0.21 ml (1.4 millimole) of 2-piperidino-1,3,2-dioxaphospholane were added to a solution of 2.4 g (5 millimoles) of penicillin-G-sulfoxide-trichloroethylester in 70 ml dry dioxane. The procedure disclosed in Example 1 was followed. A crude product was obtained containing the desired compound in a yield corresponding to 52%. NMR and IR spectra showed the same characteristic signals as set forth in Example 1.

EXAMPLE 3

Trichloroethyl-3-methyl-7-phenylacetamido-ceph-3-em-4-carboxylate 0.45 ml of a 2.2N methylene chloride solution of α-picoline-hydrobromide (1 millimole) and 0.24 ml (1 millimole) of piperidino-diphenylphosphine were added to a solution of 2.4 g (5 millimoles) of penicillin-G-sulfoxide-trichloroethylester in 70 ml dioxane.

The procedure described in Example 1 was followed, except that the mixture was refluxed for 6 ½ hours. An amorphous, crude product was obtained. By NMR spectroscopy, it was found that said product contained the desired compound in an amount corresponding to 59% of the theoretical amount.

NMR and IR spectra showed the same characteristic signals as set forth in Example 1.

EXAMPLE 4

Trichloroethyl-3-methyl-7-phenoxyacetamido-ceph-3-em-4-carboxylate 2.5 g (5 millimoles) of penicillin-V-sulfoxide-trichloroethylester were dissolved in 70 ml dioxane, and 0.45 ml of a 2.2N methylene chloride solution of α-picoline-hydrobromie (1 millimole), 0.10 ml (1 millimole) of α-picoline, and 0.24 ml (1 millimole) of piperidino-diphenylphosphine were added. The procedure described in Example 1 was followed, except that the solution was refluxed for 7 hours.

A crude product (2.4 g) was obtained. By NMR spectroscopy this product showed a content of the desired compound corresponding to 47% of the theoretical amount.

NMR (CDCl$_3$): 6.8 – 7.5 (multiplet, 6H), 5.80 (dd, 1H), $J_{HNCH}$ = 9.5 Hz, $J_{HCCH}$ = 4.5 Hz, 5.00 (d, 1H), $J_{HCCH}$ = 4.5 Hz, 4.85 (AB, 2H), 4.50(S, 2H) 3.35 (AB, 2H), 2.12 (S, 3H).

IR (CHCl$_3$): 1785 cm$^{-1}$ (β-lactame CO), 1738 cm$^{-1}$ (ester CO), 1690 cm$^{-1}$ (amide I), 1520 cm$^{-1}$ (amide II).

EXAMPLE 5

Trichloroethyl-3-methyl-7-phenoxyacetamido-ceph-3-em-4-carboxylate

The method disclosed in Example 4 was repeated with the exception that instead of 1 millimole piperidino-diphenylphosphine, 0.10 ml (0.7 millimole) of 2-piperidino-1,3,2-dioxaphospholane was used. The reaction was completed in 7 hours.

By NMR spectroscopy of the crude product, it was found that the yield was 47% of the theoretical amount.

After treatment of the crude product with a mixture of ethylether and methanol (10:1), a pure crystalline substance was obtained. Melting point: 114° – 115° C.

The spectroscopic data correspond to those set forth in Example 4.

Analysis: Calculated for C$_{18}$H$_{17}$N$_2$O$_5$SCl$_3$ C: 45.07%; H: 3.58%; N: 5.84%; S: 6.68%; Cl: 22.17% Found: C: 45.06%; H: 3.4%; N: 5.76%; S: 6.79%; Cl: 22.46%

EXAMPLE 6

Trichloroethyl-3-methyl-7-phenoxyacetamido-ceph-3-em-4-carboxylate

The method set forth in Example 4 was repeated with the exception that 0.10 g (0.5 millimole) of 2-(1'-imidazolyl)-4,5-benzo-1,3,2-dioxaphospholane was used instead of 1 millimole piperidino-diphenylphosphine. After a reaction time of 12 ½ hours, a reaction product was obtained corresponding to a yield of 32% of the theoretical amount as determined by NMR spectroscopy of the crude product.

IR and NMR spectra show the characteristic absorptions set forth in Example 4, and also some absorption of by-products.

EXAMPLE 7 p-Nitrobenzyl-3-methyl-7-phenoxyacetamido-ceph-3-em-4-carboxylate 2.5 g (5 millimoles) of penicillin-V-sulfoxide-p-nitrobenzylester are dissolved in 70 ml dry dioxane, and 0.45 ml of a 2.2N methylene-chloride solution of α-picoline hydrobromide (1 millimole), 0.05 ml (0.5 millimole) of α-picoline, and 0.10 ml (0.7 millimole) of 2-piperidino-1,3,2-dioxaphospholane are added.

The procedure set forth in Example 1 was followed, except that the mixture was refluxed for 6 hours. During the further treatment, chloroform was used instead of ethyl acetate.

NMR spectroscopy of the crude product showed that the yield of the desired compound was 51% of the theoretical amount. By treating the crude product with ethyl acetate and ether, a white crystalline pure substance was obtained. Melting point: 188° – 189° C.

NMR (CDCl$_3$): 7.85 (A$_2$B$_2$, 4H), 6.75–7.5 (m, 6H), 5.83 (dd, 1H), $J_{HNCH}$ = 9.7 Hz, $J_{HCCH}$ = 4.5 Hz, 5.30 (S, 2H), 4.98 (d, 1H), J = 4.5 Hz, 4.50 (S, 2H), 3.35 (AB, 2H), 2.12 (S, 3H).

IR (KBr): 1770 cm$^{-1}$ (β-lactame CO), 1710 cm$^{-1}$ (ester CO), 1660 cm$^{-1}$ (amide I), 1515 cm$^{-1}$ 1 (amide II).

Analysis: Calculated for C$_{23}$H$_{21}$N$_3$O$_7$S: C: 57:14%, H: 4.38%; N: 8.69%; S: 6.63% Found: C: 56.59%; H: 4.41%; N: 8.64%; S: 6.65%.

EXAMPLE 8 p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.065 ml (1 millimole) of methane sulfonic acid, 0.10 ml (1 millimole) of α-picoline, and 0.09 ml (0.5 millimole) of 2-piperidino-4,5-benzo-1,3,2-dioxaphospholane were added. The procedure set forth in Example 7 was followed, except that the mixture was refluxed for 6 ¼ hours. After evaporation of the chloroform solution and treating the residue with ethyl acetate-ether, 1.2 g (50%) of a white crystalline substance were obtained. Melting point: 187° – 189° C.

NMR and IR spectra show the same characteristic signals as stated in Example 7.

Analysis: Calculated for C$_{23}$H$_{21}$N$_3$O$_7$S: C: 57.14%; H: 4.38%; N: 8.69%; S: 6.63%; Found: C: 56.88%; H: 4.44%; N: 8.66%; S: 6.65%.

Treatment of the mother liquid yielded further 3% of the desired compound.

COMPARISON EXAMPLE I p-Nitrobenzyl3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.033 ml (0.5 millimole) of methane sulfonic acid, and 0.05 ml (0.5 millimole) of α-picoline were added.

The procedure set forth in Example 7 was followed, except that the mixture was refluxed for 15 ¼ hours. The further treatment was made difficult due to an oily layer precipitated on the interior of the reaction flask. Since the precipitated substance was insoluble in chloroform, ethylacetate and dimetylsulfoxide, it was not used in the further procedure.

NMR spectroscopy of the crude product obtained by the above-mentioned procedure contained the desired product in an amount corresponding to 48% of the theoretical amount.

NMR and IR spectra showed the same characteristic signals as set forth in Example 7.

EXAMPLE 9 p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.31 g (1 millimole) of pyridinium-tri-chloroethylphosphate, 0.04 ml (0.5 millimole) of pyridine, and 0.09 ml (0.5 millimole) of 2-piperidino-4,5-benzo-1,3,2-dioxaphospholane were added. The procedure set forth in Example 7 was followed, except that the mixture was refluxed for 6 hours. NMR spectroscopy of the crude product showed a yield corresponding to 64% of the theoretical amount.

After crystallization in ethyl acetate-ether, 1.3 g (54%) of a white crystalline and pure substance was obtained. Melting point: 189° – 190° C.

NMR and IR spectra showed the same characteristic signals as set forth in Example 7.

Analysis: Calculated for $C_{23}H_{21}N_3O_7S$: C: 57.14%; H: 4.38%; N: 8.69%; S: 6.63%; Found: C: 56.77%; H: 4.39%; N: 8.62%; S: 6.59%.

COMPARISON EXAMPLE II p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dioxane, and 0.15 g (0.5 millimole) of pyridinium-trichloroethylphosphate was added.

The procedure set forth in Example 7 was followed, except that the reaction mixture was refluxed for 11 ¼ hours.

NMR spectroscopy of the crude product showed a yield of the desired product in an amount of 43% of the theoretical amount.

NMR and IR spectra show the characteristic signals which are set forth in Example 7.

After recrystallization from ethyl acetate-ether, the product was still brown. Melting point: 175° – 180° C.

EXAMPLE 10 p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.20 g (1 millimole) of N,N-dimethylaniline, hydrobromide, 0.06 ml (0.5 millimole) of N,N-dimethylaniline, and 0.075 ml (0.5 millimole) of 2-piperidino-1,3,2-dioxaphospholane were added.

The procedure set forth in Example 7 was followed, except that the reaction mixture was refluxed for 5 hours.

NMR spectroscopy of the crude product showed a yield of the desired substance in an amount corresponding to 40% of the theoretical amount.

A crystalline white and pure substance was obtained from the crude product by treatment with ethyl acetate-ether. Melting point: 188° – 189° C.

Analysis: Calculated for $C_{23}H_{21}N_3O_7S$: C: 57.14%; H: 4.38%; N: 8.69%; S: 6.63%; Found: C: 56.59%; H: 4.34%; N: 8.65%; S: 6.65%.

NMR and IR spectra show the same characteristic signals as stated in Example 7.

EXAMPLE 11 p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.03 ml (0.5 millimole) of methane sulfonic acid, 0.6 ml (0.6 millimole) of α-picoline, and 125 mg (0.5 millimole) of 2-(2',6'-dimethylpiperidino)-4,5-benzo-1,3,2-dioxaphospholane were added.

The procedure set forth in Example 7 was followed, except that the reaction mixture was refluxed for 8 hours.

NMR spectroscopy of the crude product showed a yield of the desired product in an amount of 52% of the theoretical amount.

1.1 g (46%) of a crystalline white and pure substance was obtained by crystallization by treatment with ethyl acetateether. Melting point: 189° – 190° C.

Analysis: Calculated for $C_{23}H_{21}N_3O_7S$: C: 57.14%; H: 4.38%; N: 8.69%; S: 6.63%; Found: C: 56.72%; H: 4.34%; N: 8.67%; S: 6.64%.

NMR and IR spectra showed the same characteristic signals as stated in Example 7.

EXAMPLE 12 p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.45 ml of a 2.2N methylene chloride solution of α-picoline hydrobromide (1 millimole), 0.05 ml (0.5 l millimole) of α-picoline, and 0.09 ml (0.5 millimole) of tris-(dimethyl-amino)-phosphine were added. The procedure set forth in Example 7 was followed, except that the mixture was refluxed for 6 hours. NMR spectroscopy of the crude product showed a yield of the desired substance in an amount corresponding to 46% of the theoretical amount. 0.91 g (38%) of a crystalline white and pure substance was obtained by treating the crude product with ethyl acetate-ether. Melting point: 187° – 189° C.

Analysis: Calculated for $C_{23}H_{21}N_3O_7S$: C: 57.14%; H: 4.38%; N: 8.69%; S: 6.63%; Found: C: 56.85%; H: 4.39%; N: 8.70%; S: 6.65%.

NMR and IR spectra showed the same characteristic signals as set forth in Example 7.

COMPARISON EXAMPLE III p-Nitrobenzyl-3-methyl-7-phenoxyacetamido-ceph-3-em-4-carboxylate 2.5 g (5 millimoles) of penicillin-V-sulfoxide-p-nitrobenzylester were dissolved in 70 ml dry dioxane, and 0.45 ml of a 2.2N methylene chloride solution of α-picoline hydrobromide (1 millimole), and 0.10 ml (1 millimole) of α-picoline were added.

The procedure followed was as set forth as in Example 7, except that the reaction mixture was refluxed for 7 hours. NMR spectroscopy of the crude product showed a yield of 24% of the desired substance.

EXAMPLE 13 p-Nitrobenzyl-3-methyl-7-phenoxyacetamido-ceph-3-em-4-carboxylate 10 g (20 millimoles) of penicillin-V-sulfoxide-p-nitrobenzylester were slurried in 70 ml dry dioxane, and 0.70 g (4 millimoles) of α-picoline hydrobromide, 0.20 ml (2 millimoles) of a α-picoline, and 0.31 ml (2 millimoles) of 2-piperidino-1,3,2-dioxaphospholane were added.

The reaction mixture was heated, and before the boiling point was reached, everything had been dissolved. The reaction mixture was refluxed for 5 hours, and the reflux was passed through 35 g basic aluminum oxide. The siccative was saturated with dioxane before the heating was initiated. The reaction was followed on T.L.C. which after a period of 4 ½ hours showed that the reaction had been completed.

After the completion of the reaction, the major part of the dioxane was removed in vacuum. The concentration caused the product to crystallize. In order to remove the catalyst and residue of the solvent, the product obtained was dissolved in 100 ml chloroform and washed 3 times with 150 ml ice water. The organic phase was dried with magnesium sulfate and evaporated in vacuum. The crude product thus obtained contained the desired substance in an amount corresponding to 60% of the theoretical amount. After treating the crude product with ethyl acetateether, 4.85g(50%) of a white crystalline pure substance was obtained. Melting point: 189° – 190° C.

Analysis: Calculated for $C_{23}H_{21}N_3O_7S$: C: 57.14%; H: 4.38%; N: 8.69%; S: 6.63%; Found: C: 56.89%; H: 4.44%; N: 8.61%; S: 6.70%.

NMR and IR spectra show the same characteristic signals as set forth in Example 7.

When further purifying the mother liquid, an additional amount of the desired substance corresponding to 8% of the theoretical amount was obtained.

EXAMPLE 14 p-Nitrobenzyl-3-methyl-7-phenoxyacetamido-ceph-3-em-4-carboxylate

A. The procedure set forth in Example 13 was repeated, except that calcium chloride was used instead of basic aluminum oxide. Yield: 59%; Melting Point: 188° – 189° C.

B. The procedure set forth in Example 13 was repeated, except that sodium hydroxide pellets were used instead of basic aluminum oxide. The yield obtained was 55% of the theoretical amount. Melting point: 188° – 189° C.

C. The procedure set forth in Example 13 was repeated, except that a 4A° molecular sieve was used instead of basic aluminum oxide. The yield obtained was 55% of the theoretical amount. Melting point: 189° – 190° C.

EXAMPLE 15 p-Nitrobenzyl-3-methyl-7-phenoxyacetamido-ceph-3-em-4-carboxylate

A. The procedure set forth in Example 13 was repeated, except that 70 ml toluene was used instead of 70 ml dioxane. The reaction mixture was refluxed at 114° C for 3.5 hours. The yield obtained was 41% of the theoretical amount. Melting point: 189° – 191° C.

B. The procedure set forth in Example 13 was repeated, except that 100 ml methylisobutylketone were used instead of 70 ml dioxane. The reaction mixture was refluxed at 120° C for 1 ½ hours. The product which crystallized when the solution was concentrated, was obtained in a yield of 33% of the theoretical amount. Melting point: 188° – 190° C.

EXAMPLE 16 p-Nitrobenzyl-3-methyl-7-phenoxyacetamido-ceph-3-em-4-carboxylate 10 g (20 millimoles) of penicillin-V-sulfoxide-p-nitrobenzylester were slurried in 70 ml dioxane, and 0.70 g (4 millimoles) of α-picoline hydrobromide, 0.10 ml (1 millimole) of α-picoline, and 0.15 ml (1 millimole) of 2-piperidino-1,3,2-dioxaphospholane were added.

The procedure followed was as set forth in Example 13, except that 0.15 ml of 2-piperidino-1,3,2-dioxaphospholane were added after refluxing for 2 ½ hours.

NMR spectroscopy of the crude product showed that a yield of 63% of the theoretical amount had been obtained.

4.75 g (49%) of the desired product was obtained after recrystallization. Melting point: 190° – 191° C.

Analysis: Calculated for $C_{23}H_{21}N_3O_7S$: C: 57.14%; H: 4.38%; N: 8.69%; S: 6.63%; O: 23.16%; Found: C: 56.74%; H: 4.45%; N: 8.61%; S: 6.59%; O: 23.25%.

NMR and IR spectra show the same characteristic signals as set forth in Example 7.

EXAMPLE 17 p-Nitrobenzyl-3-methyl-7-phenoxyacetamido-ceph-3-em-4-carboxylate 10 g (20 millimoles) of penicillin-V-sulfoxide-p-nitrobenzylester were slurried in 70 ml dry dioxane, and 0.70 g (4 millimoles) of α-picoline hydrobromide, and 0.48 ml (2 millimoles) of piperidino-diphenylphosphine were added. The procedure followed was as set forth in Example 13, except that the mixture was refluxed for 5 hours. By NMR spectroscopy of the crude product it was found that the desired product had been obtained in a yield of 62% of the theoretical amount.

After treating said crude product with a mixture of benzene, ethyl acetate, and ether, 5.9 g (61%) of a crystalline white pure substance were obtained. Melting point 190° – 191° C.

Analysis: Calculated for $C_{23}H_{21}N_3O_7S$: C: 57.14%; H: 4.38%; N: 8.69%; S: 6.63%; Found: C: 57.08%; H: 4.44%; N: 8.68%; S: 6.53%.

NMR and IR spectra show the same characteristic signals as set forth in Example 7.

EXAMPLE 18 p-Nitrobenzyl-3-methyl-7-phenoxyacetamido-ceph-3-em-4-carboxylate

Example 17 was repeated, except that 0.20 ml (2 millimoles) of α-picoline were added before the refluxing. The mixture was refluxed for 5 hours. By NMR spectroscopy of the crude product it was found that the desired product had been obtained in an amount corresponding to 63% of the theoretical amount. After treating the crude product with a mixture of benzene, ethyl acetate, and ether, 6.3 g (65%) of a crystalline white and pure substance were obtained.

Melting point: 190° – 191° C.

Analysis: Calculated for $C_{23}H_{21}N_3O_7S$: C: 57.14%; H: 4.38%; N: 8.69%; S: 6.63%; Found: C: 56.51%; H: 4.40%; N: 8.56%; S: 6.50%.

NMR and IR spectra show the same characteristic signals as set forth in Example 7. By a further purification of the mother liquid, an additional amount of the desired substance corresponding to 5% of the theoretical amount is obtained.

EXAMPLE 19 p-Nitrobenzyl-3-methyl-7-phenoxyacetamido-ceph-3-em-4-carboxylate 10 g (20 millimoles) of penicillin-V-sulfoxide-p-nitrobenzylester were slurried in 70 ml dry dioxane, and 0.70 g (4 millimoles) of α-picoline hydrobromide, 0.10 ml (1 millimole) of α-picoline, and 0.15 ml (1 millimole) of 2-piperidino-1,3,2-dioxaphospholane were added. The procedure followed was as set forth in Example 13, except that dry air was bubbled through the solution during the reaction and that the mixture was refluxed for 5 ½ hours.

By NMR-spectroscopy of the crude product it was found that the desired product had been obtained in a yield of 60% of the theoretical amount.

After treating said crude product with a mixture of benzene, ethylacetate and ether, 5.0 g (52%) of a crystalline white pure substance were obtained.

Melting point: 190° – 191° C.

Analysis: Calculated for $C_{23}H_{21}O_7N_3S$: C: 57.14%; H: 4.38%; N: 8.69%; S: 6.63%; Found: C: 57.08%; H: 4.47%; N: 8.52%; 6.52%.

NMR and IR spectra show the same characteristic signals as set forth in Example 7.

By a further purification of the mother liquid, 0.5 g of the desired substance corresponding to 5% of the theoretical amount is obtained.

EXAMPLE 20 p-Nitrobenzyl-3-methyl-7-phenoxyacetamido-ceph-3-em-4-carboxylate 100 g (0.2 mole) of penicillin-V-sulfoxide-p-nitrozylester were slurried in 390 ml dry dioxane, and 40 millimoles of hydrogen bromide in 110 ml of dry dioxane, 5.9 ml (60 millimoles) of α-picoline and 5.4g of piperidino-diphenylphosphine were added.

The reaction mixture was heated, and before the boiling point was reached, everything had been dissolved. The reaction mixture was refluxed for 4 hours, and the reflux was passed through 350 g basic aluminum oxide. The siccative was saturated with dioxane before the heating was initiated.

After the completion of the reaction, the major part of the dioxane was removed in vacuum. The product crystallized during this operation was slurried in 75 ml of ethanol and filtered off. 56.8 g (59%) of a white crystalline product were obtained. Melting point: 190° – 191° C.

Analysis: Calculated for $C_{23}H_{21}O_7N_3S$: C: 57.14%; H: 4.38%; O: 23.16%; N: 8.69%; S: 6.63%; Found: C: 56.96%; H: 4.46%; O: 22.87%; N: 8.44%; S: 6.46%.

NMR and IR spectra show the same characteristic signals as set forth in Example 7.

Further purification of the mother liquid gave 8.8 g (9%) of a white crystalline product. Melting point 189° – 191° C.

What is claimed is:

1. The process for converting a penicillin G or V sulfoxide ester to the corresponding 3-desacetoxycephalosporin ester which comprises heating a solution of the penicillin G or V sulfoxide ester in an inert solvent in the presence of a catalyst, said catalyst being the complex formed by a phosphite or phosphine amide selected from the group consisting of:
   2-piperidino-1,3,2-dioxaphospholane,
   Piperidino-diphenylphosphine,
   2-piperidino-4,5-benzo-1,3,2-dioxaphospholane,
   2-(2',6'-dimethylpiperidino-4,5-benzo-1,3,2-dioxaphospholane
   2-(1'-imidazolyl)-4,5-benzo-1,3,2-dioxaphospholane,
   tris-(dimethylamino)-phosphine.
and the salt of a strong acid with a nitrogeneous base selected from the group consisting of:
   alfa-picoline hydrobromide
   alfa-picolinium methanesulfonate
   pyridinium 2-trichloroethylphosphate
   N,N-dimethylaniline hydrobromide 2. The process of claim 1 wherein the reaction is carried out at a temperature in the range of 80° C. to 130° C.

3. The process of claim 1 wherein the molar ratio of amide to the penicillin sulfoxide is in the range of 0.04 to 0.25.

4. The process of claim 1 wherein the molar ratio of amide to the salt of nitrogeneous base is in the range of 0.2 to 2.

5. The process of claim 1 wherein the molar ratio of nitrogeneous base to acid is in the range of 1 to 2.

6. The process of claim 1 wherein the molar ratio of penicillin sulfoxide to the amide to the acid to the nitrogeneous base is 10 : 1 : 2 : 3.

7. The process as in claim 1 wherein the solvent is dioxane.

8. The process of claim 1 wherein the salt is α-picoline hydrobromide.

* * * * *